US012011564B2

(12) United States Patent
Xiao

(10) Patent No.: US 12,011,564 B2
(45) Date of Patent: Jun. 18, 2024

(54) HANDHELD TATTOO DEVICE WITH INTEGRATED BATTERY POWER SOURCE, CONTROL CIRCUITRY, AND USER INTERFACE WITH TOUCH SENSOR

(71) Applicant: Long Xiao, North York (CA)

(72) Inventor: Long Xiao, North York (CA)

( * ) Notice: Subject to any disclaimer, the term of this patent is extended or adjusted under 35 U.S.C. 154(b) by 387 days.

(21) Appl. No.: 17/397,485

(22) Filed: Aug. 9, 2021

(65) Prior Publication Data
US 2023/0040685 A1    Feb. 9, 2023

(51) Int. Cl.
*A61M 37/00*       (2006.01)
*G06F 3/0484*      (2022.01)
*G06F 3/04847*     (2022.01)
*G06F 3/0488*      (2022.01)
*G06F 3/04883*     (2022.01)
*G06F 3/0482*      (2013.01)

(52) U.S. Cl.
CPC ..... *A61M 37/0076* (2013.01); *G06F 3/04847* (2013.01); *G06F 3/04883* (2013.01); *A61M 2205/505* (2013.01); *A61M 2205/586* (2013.01); *A61M 2205/8206* (2013.01); *G06F 3/0482* (2013.01)

(58) Field of Classification Search
CPC ........ A61M 37/0076; A61M 2205/505; A61M 2205/8206; A61M 2205/586; G06F 3/04847; G06F 3/04883
See application file for complete search history.

(56) References Cited

U.S. PATENT DOCUMENTS

| 3,840,799 | A | * | 10/1974 | Macko | H02M 7/517 |
| | | | | | 318/722 |
| 4,719,825 | A | * | 1/1988 | LaHaye | A61M 37/0076 |
| | | | | | 401/172 |
| 5,814,015 | A | * | 9/1998 | Gargano | A61M 5/1456 |
| | | | | | 604/67 |
| 6,033,421 | A | * | 3/2000 | Theiss | A61M 37/0076 |
| | | | | | 606/186 |
| 6,505,530 | B2 | | 1/2003 | Adler et al. | |

(Continued)

FOREIGN PATENT DOCUMENTS

EP    3093041 B1    12/2019
WO    2021/127720 A1    7/2021

OTHER PUBLICATIONS

Extended European Search Report dated Feb. 2, 2023 issued in related European patent application No. 22188769.8 (9 pages).

*Primary Examiner* — Julian W Woo

(57) ABSTRACT

A handheld tattoo device comprises an elongated body comprising a grip section and an upper section above the grip section. The grip section comprises a coupling end configured to removably couple with a needle module comprising one or more needles. The upper section comprises a needle actuator for actuating the one or more needles through a shaft extending through the grip section, and a battery power source for supplying electrical power to the needle actuator. The device also comprises a user interface on the upper section, the user interface comprising a display and a touch sensor for detecting finger gestures of a user; and a control circuitry in the upper section for controlling the power supplied to the actuator by the battery power source based on user input received through the user interface.

27 Claims, 15 Drawing Sheets

(56) References Cited

U.S. PATENT DOCUMENTS

| | | | |
|---|---|---|---|
| 7,133,277 B2* | 11/2006 | Ikari | H04N 23/51 |
| | | | 396/539 |
| 7,969,715 B2 | 6/2011 | Copeland et al. | |
| 8,029,527 B2 | 10/2011 | Lisec | |
| 8,228,666 B2 | 7/2012 | Rickard | |
| 9,254,376 B2 | 2/2016 | Colton et al. | |
| 9,333,371 B2 | 5/2016 | Bean et al. | |
| 9,452,281 B2 | 9/2016 | Chan et al. | |
| 9,826,815 B2* | 11/2017 | Pires | A45D 40/24 |
| 10,471,246 B1 | 11/2019 | Lipscomb | |
| 10,898,704 B2* | 1/2021 | Vescovi | A61M 37/0084 |
| 11,260,209 B2* | 3/2022 | Siciliano | A61M 37/0015 |
| 11,400,268 B2* | 8/2022 | Siciliano | A61M 37/0015 |
| 2008/0300615 A1* | 12/2008 | Colton | A61M 37/0076 |
| | | | 606/186 |
| 2010/0241151 A1 | 9/2010 | Rickard | |
| 2012/0214027 A1* | 8/2012 | Ahn | H01M 10/425 |
| | | | 429/7 |
| 2014/0324089 A1 | 10/2014 | Chan et al. | |
| 2015/0164543 A1 | 6/2015 | Kluge | |
| 2017/0021154 A1 | 1/2017 | Johanson | |
| 2019/0060626 A1 | 2/2019 | Xiao | |
| 2019/0076636 A1 | 3/2019 | Lee | |
| 2019/0134371 A1 | 5/2019 | Johansson | |
| 2019/0217072 A1 | 7/2019 | Xiao | |
| 2020/0016389 A1* | 1/2020 | Wehinger | A61M 37/0076 |
| 2020/0306519 A1 | 10/2020 | Smead et al. | |
| 2021/0060325 A1 | 3/2021 | Xiao | |
| 2021/0213370 A1* | 7/2021 | Wang | H05K 7/1432 |

\* cited by examiner

HANDHELD TATTOO DEVICE WITH INTEGRATED BATTERY POWER SOURCE, CONTROL CIRCUITRY, AND USER INTERFACE WITH TOUCH SENSOR

FIELD

The present disclosure relates generally to handheld tattoo devices, particularly to handheld tattoo devices with integrated battery power source, control circuitry, and user interface.

BACKGROUND

Rotary tattoo devices typically include an electrical motor for reciprocally driving one of more needles to applying ink to the skin of a subject. The power supply unit for providing electrical power to the motor is typically separately provided and the power supply unit includes a control system for adjusting the motor speed. The control system may include a display and control buttons, knobs, or keys for the user to adjust the power settings and speeds of the motor. The power supply and control unit is typically connected to the motor on the tattoo device by a power cable so that the power supply and control unit can be placed on a desk or cart while the tattoo device is held in a hand of the operator. A foot pedal is sometimes used to control the power supply or operation of the motor.

For example, such conventional tattoo devices and their respective power supply and control units are disclosed in U.S. Pat. No. 7,969,715 to Copeland et al. and U.S. Pat. No. 8,228,666 to Rickard.

The power cable may get into the way during operation. Some tattoo devices include a built-in or integrated power source, such as a battery or battery pack on the tattoo device. A separate control device may be provided and wirelessly connected to the built-in power unit to control the operation of the power source or the motor on the tattoo device. For example, U.S. Pat. No. 9,254,376 to Colton et al. discloses a wireless, battery powered tattoo apparatus, which employs a separate and wirelessly connected voltage regulator to provide control of the motor operation of the tattoo applicator. US 2017/0021154 by Johansson discloses a tattoo machine power supply with a user interface for a tattoo machine, which wirelessly transmits to the tattoo machine activation signals based on user interaction with the user interface. US 2020/0306519 by Smead et al. discloses a compact battery and voltage supply controller apparatus for a tattoo machine configured to connect with the tattoo machine through replaceable internally received magnetic connection adapters. A toggle switch is provided to operate a display screen. U.S. Pat. No. 10,471,246 to Lipscomb discloses a wireless power supply and speed controller for a tattoo machine. An input selection assembly is positioned on an exterior surface of the battery housing. A controller is electrically connected to the input selection assembly for regulating the voltage flowing from the battery according to a speed generation signal generated by the input selection assembly.

Some existing handheld tattoo devices have a generally pen shape and are referred to as tattoo pen, tattoo pen machine, wireless tattoo machine, wireless rotary tattoo pen machine. These machines can use standard batteries such as rechargeable batteries and standard power cables such as USB or USB-C charging cables for charging the batteries. Some tattoo pen machines have built-in LED or LCD displays, a controller, and a battery housing.

However, it is desirable to improve existing tattoo devices with integrated power supply and control units.

SUMMARY

It has been recognized by the present inventor that in existing tattoo devices the power control unit is typically provided with a separate housing mounted on the battery pack or at an end of a handheld tattoo device. The added control unit or control unit housing on the handheld device makes the device more difficult to manipulate. Further, it has been recognized that the existing integrated control units on handheld tattoo devices are not very convenient to use or operate.

In an aspect of the present disclosure, there is thus provided a handheld tattoo device with an integrated battery power source, and control components with a graphical user interface having a touch sensor, such as a touchscreen.

In an embodiment, there is provided a handheld tattoo device. The device comprises an elongated body comprising a grip section, comprising a coupling end configured to removably couple with a needle module comprising one or more needles, and an upper section above the grip section, the upper section comprising a needle actuator for actuating the one or more needles through a shaft extending through the grip section, and a battery power source for supplying electrical power to the needle actuator. The device also comprises a user interface on the upper section, the user interface comprising a display and a touch sensor for detecting finger gestures of a user; and a control circuitry in the upper section for controlling the power supplied to the actuator by the battery power source based on user input received through the user interface.

In various embodiments of the device described in the preceding paragraph, the following features may be provided, either individually and separately, or in any combination thereof. The user interface may comprise a touchscreen providing both a display surface and a touch sensing surface. The battery power source may comprise a tubular casing for receiving a battery therein. The control circuitry may comprise at least one circuit board mounted around the tubular casing. Three rigid flat circuit boards may surround the tubular casing, or a deformable circular circuit board may curve around the tubular casing. The control circuitry may comprise a processor, and a processor readable medium storing thereon processor-executable instructions. The instructions when executed by the processor may cause the control circuitry to display information on the display; receive user input through the user interface; update the information displayed on the display in response to user input received through the user interface; control operation of the device based on the user input. The user input may comprise finger gestures detected through the touch sensor. The user interface may comprise a physical or virtual home button or key. The touch sensor may be positioned adjacent to the display. The device may comprise a plurality of touch sensors, which may provide a continuous sensing surface or discrete sensing surfaces. The actuator may comprise an electrical motor and the control circuitry may be configured to adjust a speed of the motor based on a detected finger gesture. The control circuitry may be configured to increase or decrease the speed of the motor by a preselected amount based on a swipe direction of the detected finger gesture. The touch sensor may be configured to detect if a swipe direction is an upward direction, a downward direction, a leftward direction, and a rightward direction. The swipe direction may be detectable in a display area of the display, or within a defined sensing area outside the display area. The display may be controlled by the control circuitry to display one or more of a status of the motor, an operation status of the device, a user setting for the device or the motor, and time information, wherein the status of the motor comprises the speed of the motor. The user interface may be controlled by the control circuitry to display user selectable items on the display and to receive user selection through the touch sensor. The control circuitry may comprise a primary control circuit, a voltage boost converter circuit, and a motor driver circuit. The primary control circuit may comprise a wireless transceiver and a controller. The motor may be a commutatorless direct-current motor, and the motor driver circuit may be configured to detect or calculate an instantaneous speed of the motor and transmit a signal indicative of the speed to the primary control circuit. The device may comprise a frame in the upper section, and the motor and the control circuitry may be both mounted on the same frame. The grip section may comprise a handle detachably coupled to the upper section. The battery power source may comprise a battery pack detachable from the upper section. The battery pack may be detachably mounted at a terminal end of the upper section and may comprise a tubular casing for receiving and housing a battery therein and a battery management circuit for managing at least discharging of the battery. The upper section may comprise a USB type-C receptacle, and the battery pack may comprise a USB type-C connector detachably received in the receptacle. The control circuitry may be configured to control an operation speed of the actuator based on a detected finger gesture, wherein the control circuitry causes the speed to increase in response to detecting a finger swipe in a first swipe direction, or to decrease in response to detecting a finger swipe in a second swipe direction opposite to the first swipe direction. The control circuitry may be configured to communicate with a dual-foot pedal switch through a wireless transceiver, wherein the dual-foot pedal switch can be used to provide control signals to the control circuitry in response being pressed by a user's foot.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

In overview, embodiments of the present disclosure include a handheld tattoo device with an elongated body, and a built-in needle actuator and built-in control circuitry and user interface for controlling the actuator and displaying information. The built-in actuator, and control circuitry and user interface are integrated with a hand grip in the same pen-like body to be held by a hand.

Further, the built-in user interface includes a display and a touch sensor positioned above the hand grip. The touch sensor provides a sensing surface for sensing hand or finger gestures of a user and generates a signal indicative of the sensed finger gesture as input to the built-in control circuitry for operating the device, including controlling operation of the actuator (including its motor) and the information displayed on the display.

Conveniently, it is not necessary to connect the handheld tattoo device to a wall socket or a table-top device by a connection cable during use. Further, the operation of the device can be controlled by the user using the user interface just above the hand grip, and the user is able to see operation status, such as the operation speed and other information, from the same user interface.

In some embodiments, the device has a compact and relatively simple construction. For example, the battery power source may include a tubular casing and the control circuitry may be provided on one or more circuit boards arranged around the tubular casing. The battery power source may be detachable and replaceable.

Figure 1A:
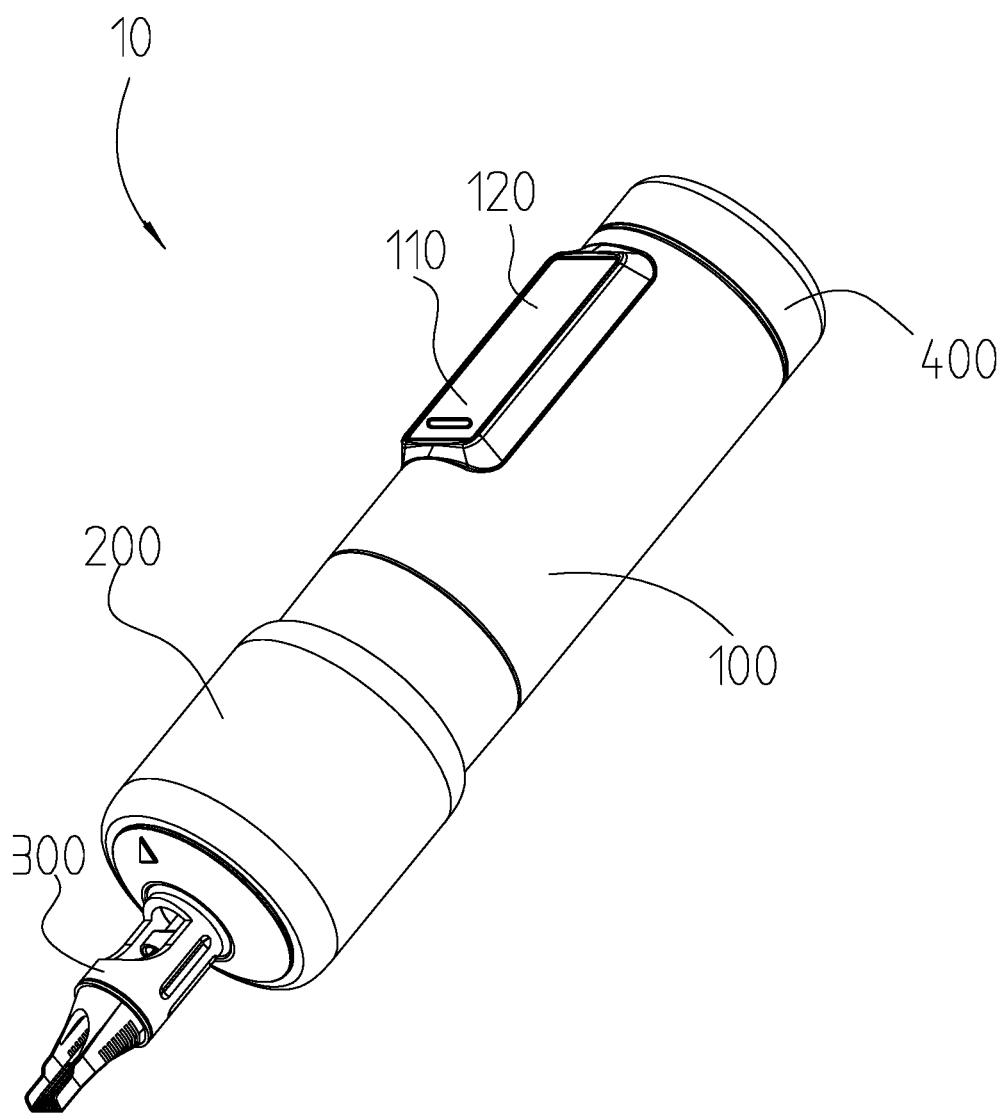
FIG. 1A is perspective view of a tattoo device, according to an embodiment of the present disclosure.

An example embodiment is illustrated in FIG. 1A, which shows a handheld tattoo device 10. As used herein, a handheld tattoo device may refer to a device commonly known as pen style tattoo device, tattoo pen, tattoo pen machine, pen tattoo machine, wireless tattoo machine, wireless rotary tattoo pen machine, or the like.

Tattoo device 10 has an elongated body, and a needle module 300 detachably coupled to the body. The elongated body may have a generally cylindrical shape. The entire device 10 may be shaped to look like a pen with a handle. The body of the device 10 has an upper section 100 and a hand grip section 200 with a coupling end 250 (see FIG. 2). The coupling end 250 is configured for coupling with needle module 300. As depicted, the upper section 100 is above the grip section 200, and the coupling end 250 is at the lower end of grip section 200. The upper section 100 includes a touchscreen thereon providing both a sensing surface 110 and a display 120, and a detachable battery pack 400 at a terminal end thereof.

The upper section 100 may provide a base unit for the device 10, and may include a needle actuator, a control circuitry, and a user interface including a touch-screen, as will be further described in detail below. Upper section 100 may include a device sometimes referred to as a tattoo machine, which may include actuation or driving components for actuating movement of the needle(s) in the needle module 300.

In the embodiment depicted in FIG. 1A, upper section 100 also includes a replaceable battery power source, such as battery pack 400, and a built-in control circuitry (see further details below) for powering and controlling the operation of the actuator and other operations of the device 10.

A needle actuator 101 (not visible in FIG. 1A, but see FIGS. 4, 5, 9A, 9B, and 10) typically includes an electric motor 160 and a motion conversion mechanism 170 for converting rotation motion to linear motion for driving reciprocal movement of the needle(s) in the attached needle module 300, through a driving connection that passes through the grip section 200.

The actuator 101 in device 10 and its connection to the needle module 300 through the grip section 200 may be provided by any suitable technology. Example technologies may include those for known rotary tattoo devices, such as disclosed in U.S. Pat. No. 6,505,530, US 20190134371, U.S. Pat. No. 8,029,527, and US 20190060626, and in co-pending U.S. patent application Ser. No. 16/814,738 by Xiao, the entire contents of which are incorporated herein by reference. Suitable actuators used in other conventional handheld tattoo devices, such as tattoo pens, may also be adapted for use in device 10.

The grip section 200 may be detachably connected to the upper section 100, or may be integrally formed with a portion of the upper section 100.

In some embodiments, grip section 200 and upper section 100 may be separately provided or sold. In other embodiments, grip section 200 and upper section 100 may be provided, such as sold or purchased, together. In some embodiments, grip section 200 and upper section 100 may be provided as an integrated unit and are not separable during use.

Grip section 200 may be provided or obtained as a separate handle piece, or integrally formed with at least a part of the upper section 200, and may be shaped and sized so the grip section 200 is suitable and convenient to be held in an operator's hand and used to perform tattoo operations.

Grip section 200 may be configured and constructed according to any suitable techniques, including those known to persons skilled in the art. An example handle described in US 2019/0060626 by Xiao may be adapted for use in or as grip section 200. The entire contents of US 2019/0060626 are incorporated herein by reference. Other suitable hand grips or handles may also be used.

Grip section 200 may have an ergonomic outer shape and dimension, and may be designed to allow precise and convenient manipulation of the device 10 during use.

Figure 2:
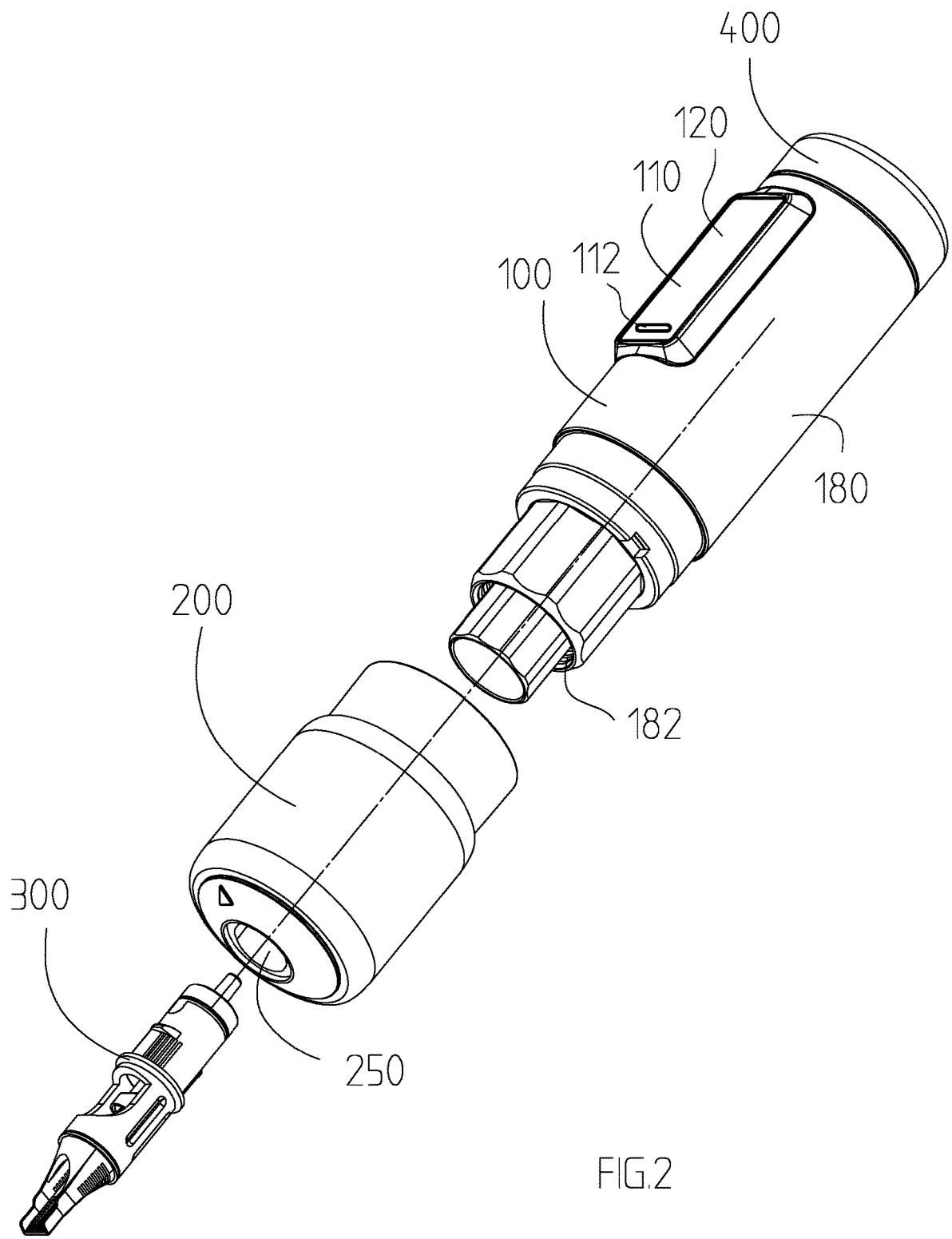
FIG. 2 is an exploded view of the tattoo device of FIG. 1A.
Figure 3:
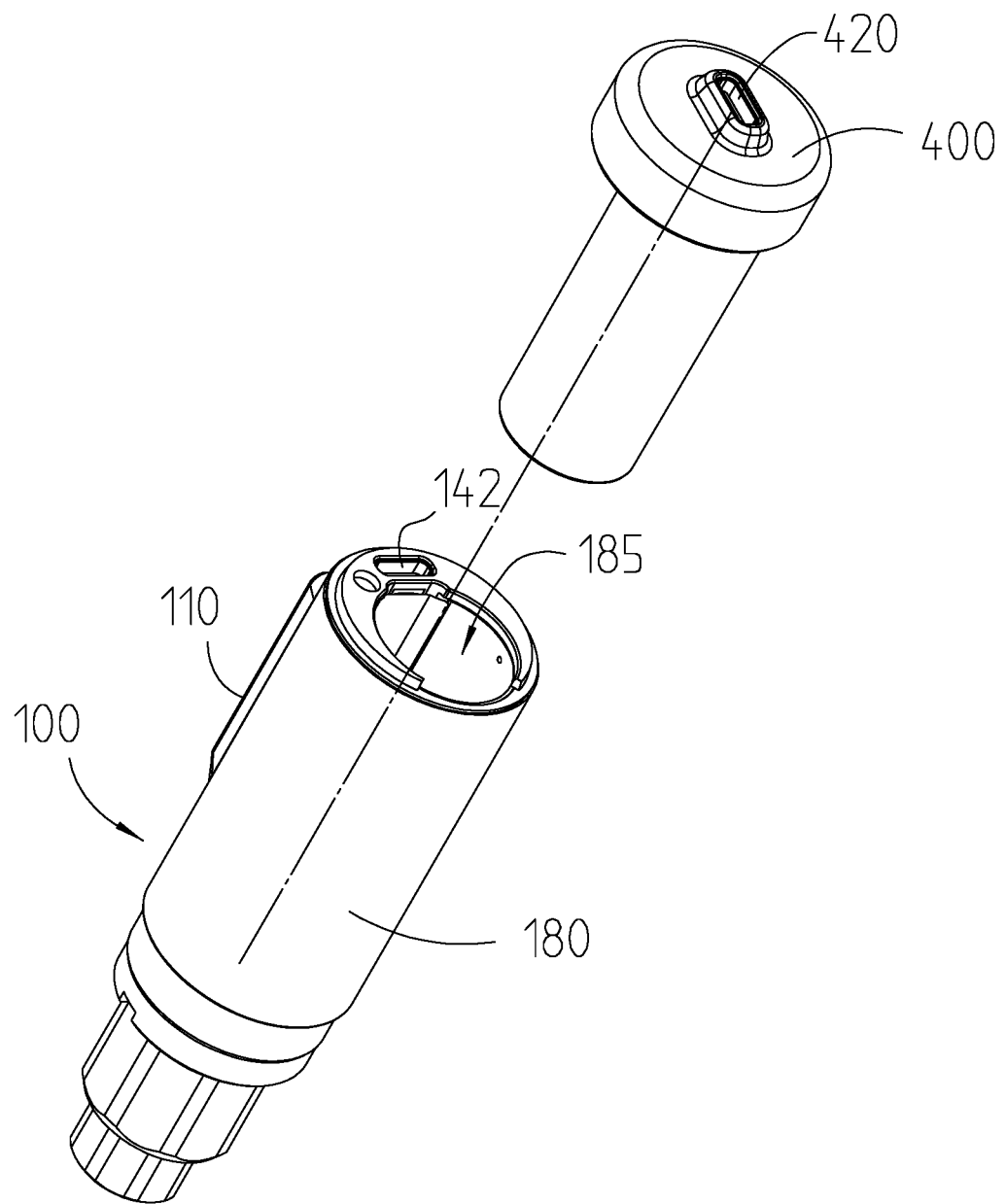
FIG. 3 is an exploded view of the battery and control section of the tattoo device of FIG. 1A.
Figure 4:
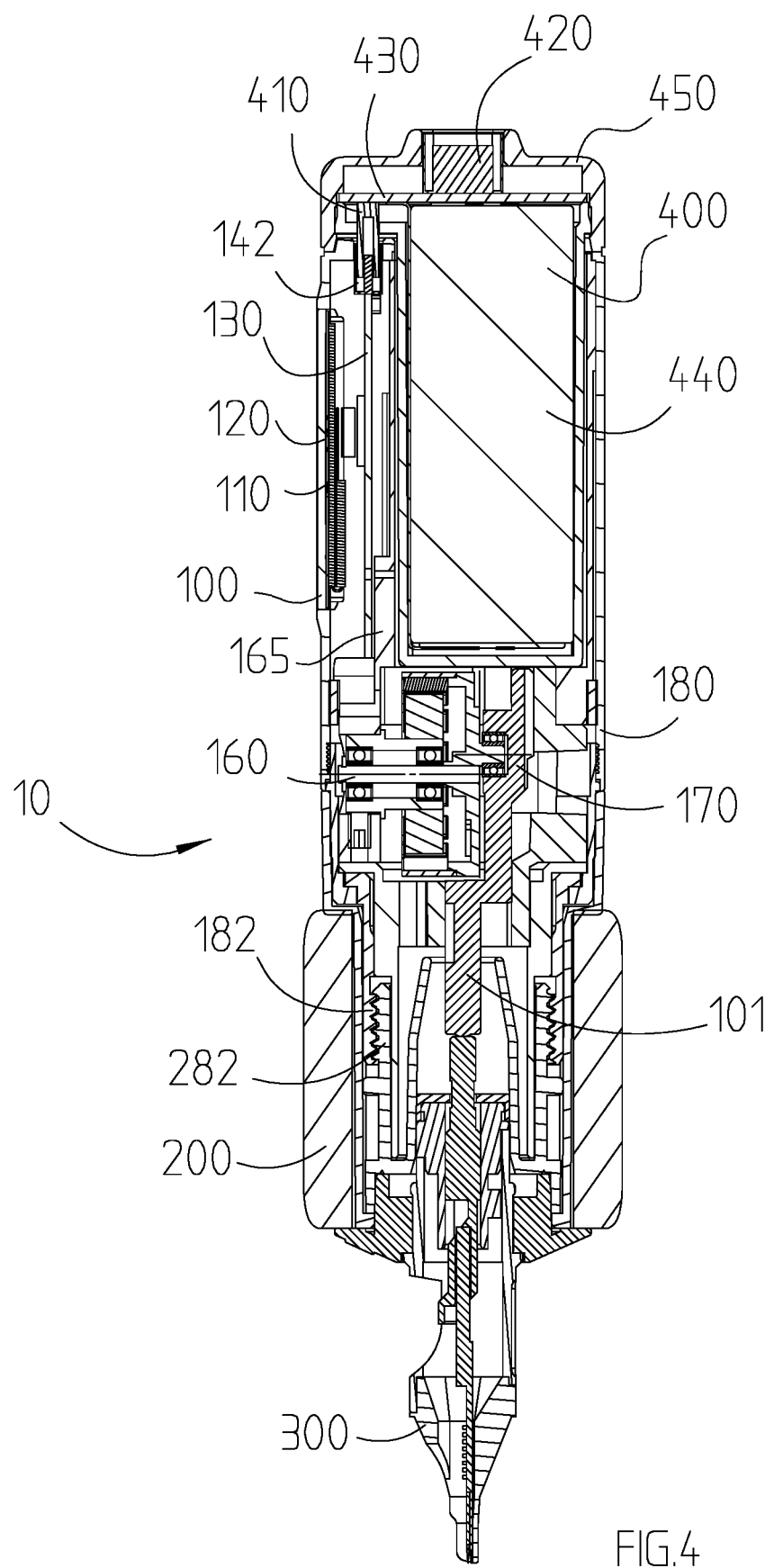
FIG. 4 is a cross-sectional view of the tattoo device of FIG. 1B along line 4-4.

In some embodiments, upper section 100 and grip section 200 are separate and removably coupled. For example, as illustrated in FIGS. 2 and 4, the upper section 100 may include a casing 180 and a threaded tubular section 182; and grip section 200 may have a corresponding and matching threaded tubular section 282 (see FIG. 4) for threaded coupling with the threaded tubular section 182 of upper section 100.

The upper section 100 (including battery pack 400), grip section 200, and coupling end 250 may provide a device or unit sometimes referred to in the art as a grip-machine combination tattoo machine.

The needle module 300 may be any suitable needle module, and can be a known or commercially available needle module and is connected to the upper section 100 through the grip section 200 and coupling end 250. Typically, needle module 300 may be separately provided to a user and may be connected to the grip section 200 before use. The needle module 300 is typically disposable after use. A plurality of interchangeable needle modules may be provided for use during a single or different tattooing sessions.

Needle module 300 may include any modular needle devices, such as devices referred to as needle cartridges. One or more removable needles may be mounted in the needle module. An example suitable needle module is described in US 2019/0217072 by Xiao, the entire contents of which are incorporated herein by reference.

As the details of the hand grip section 200, needle module 300, and the actuator for actuating the needle(s) in the needle module 300 are not the focus of the present disclosure, they are not described in detail herein. It suffices to note here that needle module 300 is typically a single-use disposable component, grip section 200 may be a single- or multiple-use disposable component, but in example embodiments, the upper section 100 of the device 10 including the battery housing is typically used for any number of tattoo sessions, although the battery or battery pack may be replaced at any time. In some embodiments, replacement of the battery may be achieved by replacing the entire battery pack 400 with a replacement battery pack containing a fully charged battery. Therefore, upper section 100 may be considered a base unit of the device 10, while other components of the device 10, such as grip section 200, needle module 300, and battery pack 400 may be replaceable components or units.

It can be appreciated that while a grip section 200 is provided, in some embodiments, device 10 may be suitable for holding by a user at the upper section 100. For example, a portion of the upper section 100 may be shaped for such purpose.

The description below focuses on the structures of upper section 100, particularly the integrated or built-in power source, control circuitry, and user interface.

Figure 1B:
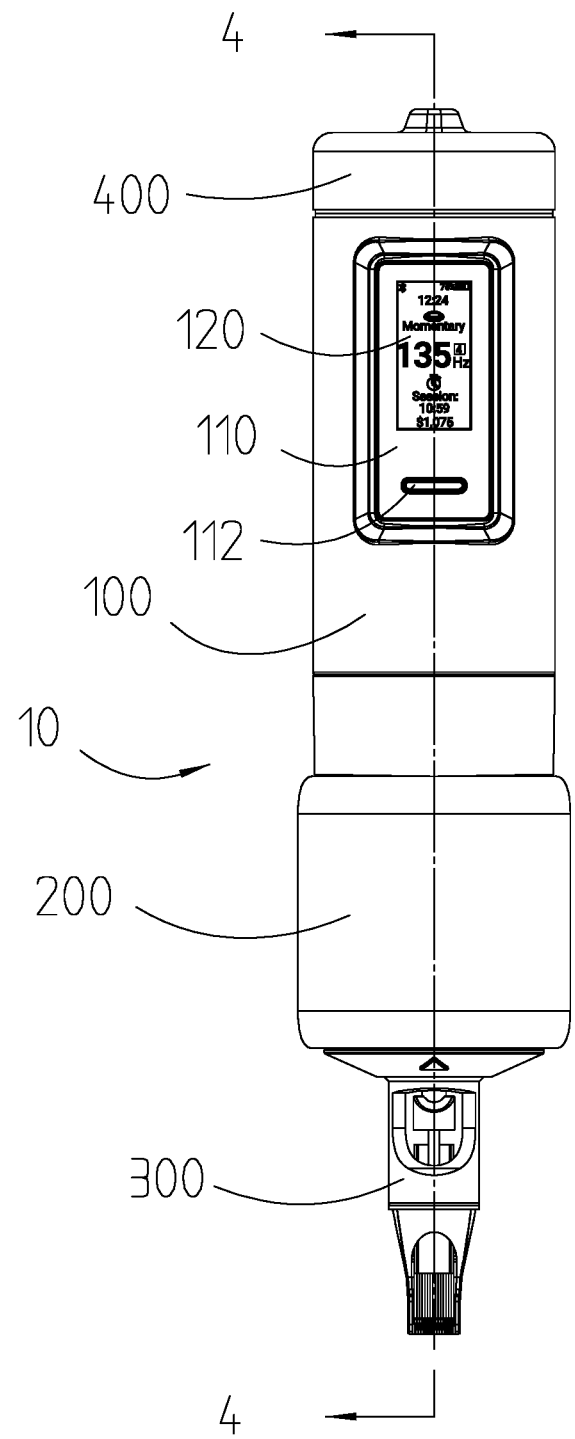
FIG. 1B is top view of the tattoo device of FIG. 1A.

Distinct from conventional handles for tattoo machines, embodiments of device 10 include a built-in control circuitry and a built-in user interface device. As illustrated in FIG. 1B, the built-in user interface device includes a touch-screen, which provides both the sensing surface 110 and display 120.

Since the device 10 is to be held in a hand, the sizes, e.g., diameter and length of the elongated body, of the device 10 are limited, which means that the surface area available for display and sensing is limited. Thus, using a touch-screen to provide both the display and the sensing area is beneficial. However, in some embodiments, the display area and sensing area may be separate.

Given the limited display area, it is also beneficial to carefully select the information to be displayed and optimize the arrangement of the information displayed on the display 120. It is further beneficial to simplify the finger gestures that can be used to provide user inputs, so that the finger gestures can be accurately and correctly detected within the limited sensing area.

For example, it has been realized that it is not necessary to display any menu or complicated selection information, such as selection keys, buttons, or bars, on the display 120. It is not necessary, and may be impractical, to provide a virtual keyboard in the display area of display 120. Rather, for example, a value of a speed of the motor in the actuator may be displayed, and touching the displayed value would trigger a prompt for input of a new speed value, which may be indicated by simply swipe across the display surface (also the sensing surface) in a direction that is pre-associated with a direction of the change in the motor speed. For example, if the swipe direction is upwards or to the right, the motor speed may be increased such as by a pre-defined amount or increment, and if the swipe direction is downwards or to the left, the motor speed may be decreased. Alternatively, two or more arrows may be shown beside, or on opposite sides of, the displayed speed value, and touching a particular arrow would increase or decrease the motor speed depending on the direction of the arrow, or the location of the arrow. Similar arrangement may be provided for other operation parameters.

In an embodiment, the touchscreen device may be an integrated on-cell capacitive touchscreen, such as a display available under the trademark AMOLED™, which has a 0.95" display area and 120×240 pixel resolution.

The sensing surface 110 may overlap with the display area of display 120, or may be adjacent to, adjoins, or surrounds the display area. In some embodiments, the sensing surface 110 and display area overlap, which as discussed can better utilize the available surface area on the device body.

Sensing surface 110 is configured to detect or sense finger gestures of a user by touching the sensing surface 110. Sensing surface 110 may be in a single continuous area, or may include multiple different areas or sections. Sensing surface 110 may be provided by a single sensor or device, or multiple sensors or sensing devices (not separately shown).

The sensor or sensing device may be a capacitive sensor, piezoelectric sensor, piezoionic sensor, or resistive sensor. Known sensors or sensing devices for touch sensing with suitable sizes and dimensions may be used.

In some embodiments, a single control button or key, which may be a physical button or key, or a virtual key, may be separately provided. As illustrated in FIGS. 1A and 1B, a physical button 112 is provided below the touchscreen that provides the sensing surface 110 and display 120. The button 112 may be used as an on/off switch to turn the device 10 on or off. Button 112 may also be used to receive other user input or selection in conjunction with sensing surface 110, and form a part of the physical user interface in device 10. Button 112 may be a mechanical button that physically moves when pressed, or a touch button without noticeable mechanical movement when pressed. Button 112 may also be provided in a separate touch area, or within the sensing surface 110 as depicted in the drawings.

In the depicted embodiment, button 112 is provided as a separate touch button within the sensing surface 110 as illustrated in FIG. 1B. As depicted in FIG. 1B, the touch area for button 112 may be indicated by a button or key sign or icon.

In some embodiments, button 112 may be used to provide multiple input commands depending on the length of the press and the press intervals. For example, a long press over a period of 1.5 seconds may be interpreted as an OFF command for turning the device 10 off. A short single press may provide a "selection" or "return" function, depending on the contents shown on the display 120. Consecutive touches within a predefined time interval may indicate another command, such as switching display pages or going to a "setting" page. Button 112 may in some embodiments function as the "Home" button (or home key) as commonly used in mobile devices such as mobile phones or computer tablets. For example, when the display 120 shows a home page, double click of button 112 may bring up the main setting page or a navigation page. In the setting or navigation page, where one of a number of listed items is highlighted or at a cursor position, a click of button 112 may select the highlighted item and bring up a specific setting page for the selected item, such as the speed of the motor. In the specific setting page, a single click of button 112 may return to the previous page. Other arrangement or functions and uses of button 112 are also possible as can be understood by those skilled in the art.

As illustrated in FIGS. 3, 4, 11 and 12, the battery pack 400 may include a casing 450 for receiving a battery 440 therein. Casing 450 thus provides a battery housing for the battery 440. The battery 440 may be any suitable battery such as a lithium battery and may be a rechargeable battery. The battery may have an initial stated operating voltage of 4.2V, a nominal Voltage of 3.7V, and may provide an output voltage in the range of about 3.0 V to about 4.2 V. To reduce the room required by the battery or batteries, a single battery cell may be used and device 10 may also include a voltage boost converter (not separately shown in FIGS. 3 and 4 but see converter 140 in FIGS. 9A and 13), which may be provided in the control circuit or in a separate power management circuit. In some embodiments, the boost converter 140 may provide an output voltage of about 9 V to about 12 V, which is the standard voltage range for various tattoo devices. The boost converter 140 may also be used to separately boost the power voltage supplied to the control circuitry, such as to about 5 V.

Figure 11:
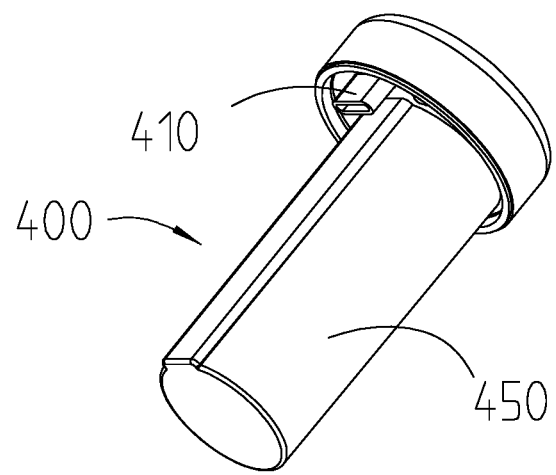
FIG. 11 is a perspective view of the battery pack of FIG. 7.
Figure 12:
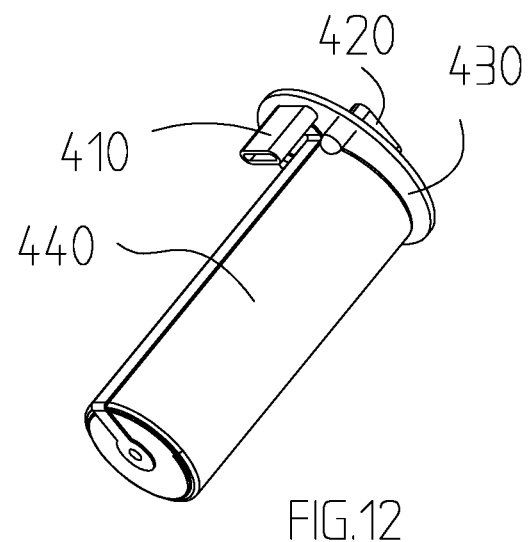
FIG. 12 is a perspective view of the battery pack of FIG. 11, without the battery housing.
Figure 13:
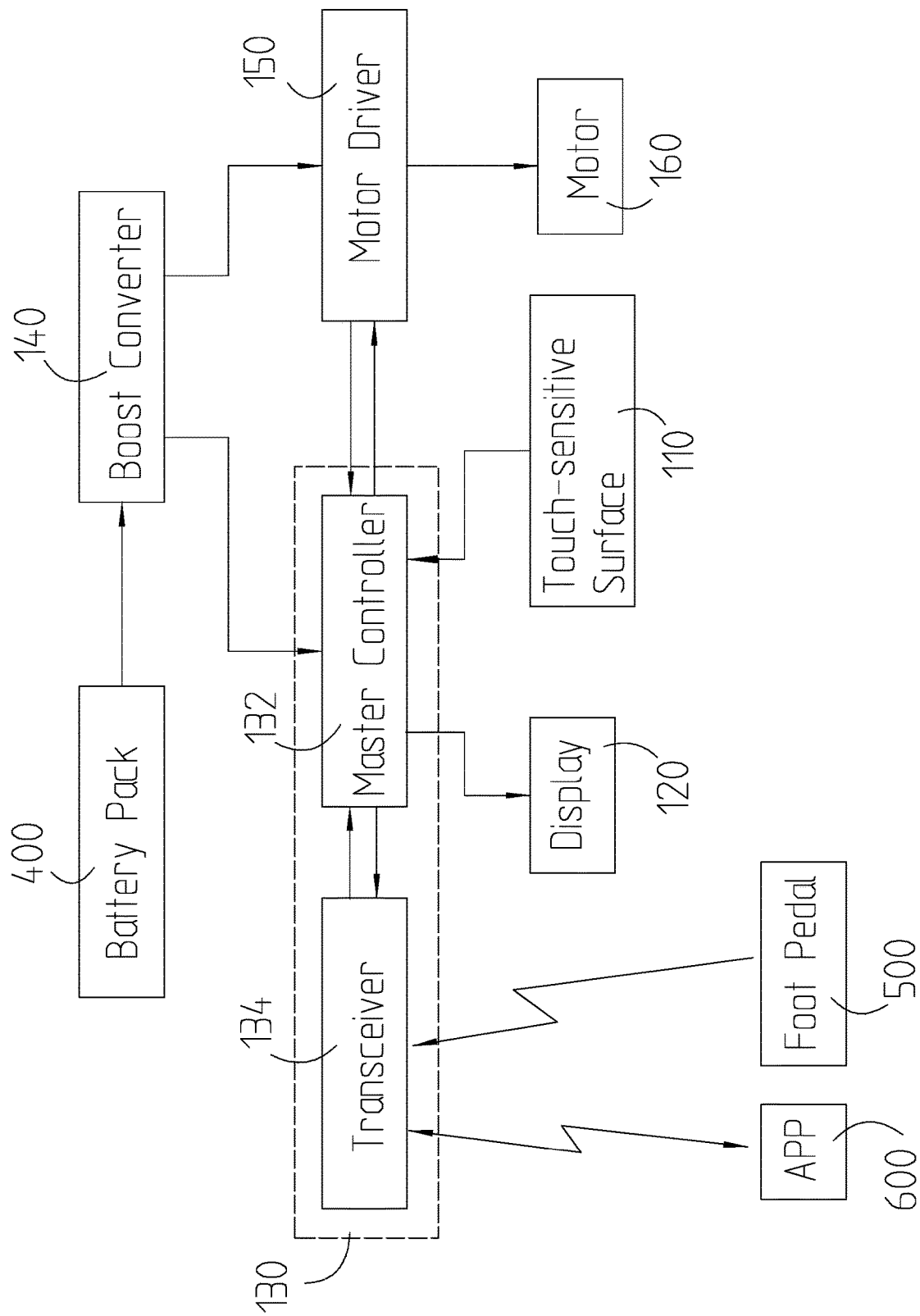
FIG. 13 is a block diagram illustrating the components of the tattoo device of FIG. 1A and their inter-connections.

As further illustrated in FIGS. 11 and 12, battery 440 may include a battery cell. For example, a suitable battery is available under product model number Panasonic™ NCR18500A, which is a li-ion rechargeable battery, with the following factory specifications: length 50 mm, diameter 18 mm, nominal voltage 3.7V, nominal capacity 2040 mAh. In some embodiments, a battery protection circuit 430 may be provided to protect the battery against over-charging or over-discharging, or possible short-circuiting. The battery pack 400 may include a casing 450, which may be made of an Acrylonitrile Butadiene Styrene (ABS) plastic material. Casing 450 encases and protects battery 440 and, optionally, a circuit board for the battery protection circuit 430.

Battery pack 400 may optionally include a charging port 420, which may include a USB type-C female connector. Such a connector may be convenient as it is easy to connect the device 10 to available charging devices, stations, or outlets commonly available. Battery pack 400 also includes a discharging port 410, which may include a USB type-C male connector. The charging and discharging ports of the battery pack 400 may also include other types of electrical connectors, such as other USB connectors. In some embodiments, micro-USB B connectors may be used. In some embodiments, a two-electrode, low-voltage DC current connector may also be used for charging or discharging the battery.

Battery pack 400 may be configured to be detachably insertable into a tubular portion of the upper section 100, and may be provided as a cartridge or plug. Battery pack 400 may also function as a cover for the upper section 100. Battery pack 400 may have its own lid. The casing 450 and the tubular portion of upper section 100 may both include imbedded magnets, such as magnetic plates or blocks, for close coupling therebetween.

The control circuitry of the device 10 may include a control unit 130, as illustrated in FIGS. 4, 5, 10, and 13. Control unit 130 may be provided on one or more circuit boards, and form the primary control circuit on the device 10. As better illustrated in FIG. 13, control unit 130 is connected to the battery voltage boost converter 140 and a motor driver circuit 150. The boost converter 140 is connected to the battery pack 400. Control unit 130 is configured to provide speed control signal to motor driver circuit 150 to control the speed of the motor 160 during operation.

Motor 160 is an electrical motor and is configured and suitable for actuating the needle(s) in the needle module 300. In some embodiments, motor 160 may be a commutatorless, brushless, direct-current motor. Motor 160 may be an outrunner sensor-less motor, such as without a built-in Hall sensor.

The motor driver circuit 150 may be configured to take low current signals from the controller 130 and convert the low current signals into higher current signals for driving the motor 160. Thus, motor driver circuit 150 may act as an interface between the motor 160 and the control circuit 130. The motor driver circuit 150 may include an integrated circuit (IC) to reduce its size and footprint. For example, motor driver IC available from Allegro MicroSystems under the model number AMT49400 may be suitable. Other advanced 3-phase, sensorless, brushless DC (BLDC) motor driver with integrated power MOSFETs may also be suitable. The motor driver IC may have a size of 5 mm×6 mm. The motor driver circuit 150 may include a closed-loop speed control circuit.

The motor driver circuit 150 may be configured to detect or measure the actual instantaneous rotation speed of motor 160, or determine the actual speed based on a measured or detected signal. The motor driver circuit 150 then communicate or transmit a signal indicative of the actual motor speed to the primary control circuit 130 as feedback so that primary control circuit 130 can in response further control adjust the motor speed based on the feedback speed signal. The primary control circuit 130 can also calculate and display the speed value on the touchscreen or display 120. For example, if the actual speed is less than the set speed set by circuit 130, circuit 130 may increase the voltage provided to the motor to increase the motor speed. If the actual speed is greater than the set speed, circuit 130 may decrease the voltage provided to the motor to decrease the motor speed. In this manner, a closed feedback loop is obtained and the relationship between supplied voltage and corresponding actual motor speed can be determined and adjusted in real time so that the motor speed can be accurately set and adjusted.

By comparison, in some existing tattoo devices, the motor speed is set by setting the supplied voltage according to a fixed voltage-speed relationship, in which case the actual motor speed may or may not be the desired set speed. The difference between the set speed and the actual speed can also vary over time or in different operating conditions such as load conditions. Thus, the speed control in such existing devices is less accurate.

Processor and memory chips suitable for use in control unit 130 or other control circuitry include integrated processor and memory chips, such as AC790N chip series available from China Zhuhai Jieli Technology Co., Ltd. This chip includes an AC7901 integrated 32 bit dual-core microcontroller unit (MCU), and WIFI and Bluetooth connections, integrated voice processing (digital signal processing—DSP), graphic coding and decoding units. This chip has a size of 6.1 mm×6.1 mm.

The control circuitry may be configured to control the speed of the motor 160. For example, the control circuit 130 may include a processor and a memory or other processor-readable storage medium in communication with the processor. The memory may store thereon processor executable instructions, which when executed by the processor, cause the control circuit 130 to monitor a finger or hand gesture input through the sensing surface 110; determine a desired command for controlling the motor 160 based upon the monitored hand or finger gesture input; and control the speed of motor 160 based upon the determined desired command.

Suitable memory may include non-volatile memory.

The primary control circuit 130 may include a master controller 132 and a wireless transceiver 134. The transceiver 134 may be in communication with an external device, such as a foot pedal 500 or a computer application device (APP) 600. The foot pedal 500 may provide additional functionality and control for operating device 10 as described in US 20210060325, the entire contents of which are incorporated herein by reference. Foot pedal 500 may be used to control device 10 such as to pause the motor, or switch operation modes. The APP 600 may be a mobile device or a tabletop computer. For example, an APP run on a mobile phone may be interacting with the device 10 through transceiver 134. For example, an APP running on a mobile device 600 may be used to control the operations of device 10 or to provide an optional alternative user interface for user input and to display operation information. APP 600 may also be used to transfer and store operation information. APP 600 may also be used to provide voice control of the operation of device 10. In some embodiments, a tattooist may operate multiple devices 10 at the same time, or over different time periods, and may use the APP 600 to collect information from the multiple devices 10 and provide accounting recording, such as automatic time recordal for fee calculation and generation of invoices or bills, and historical records.

Control circuit 130 and motor drive 150 may provide open-loop or closed-loop speed control for motor 160.

As illustrated in FIGS. 14 to 17L, the display 120 may be configured to show various operation information, including the following.

Figure 14:
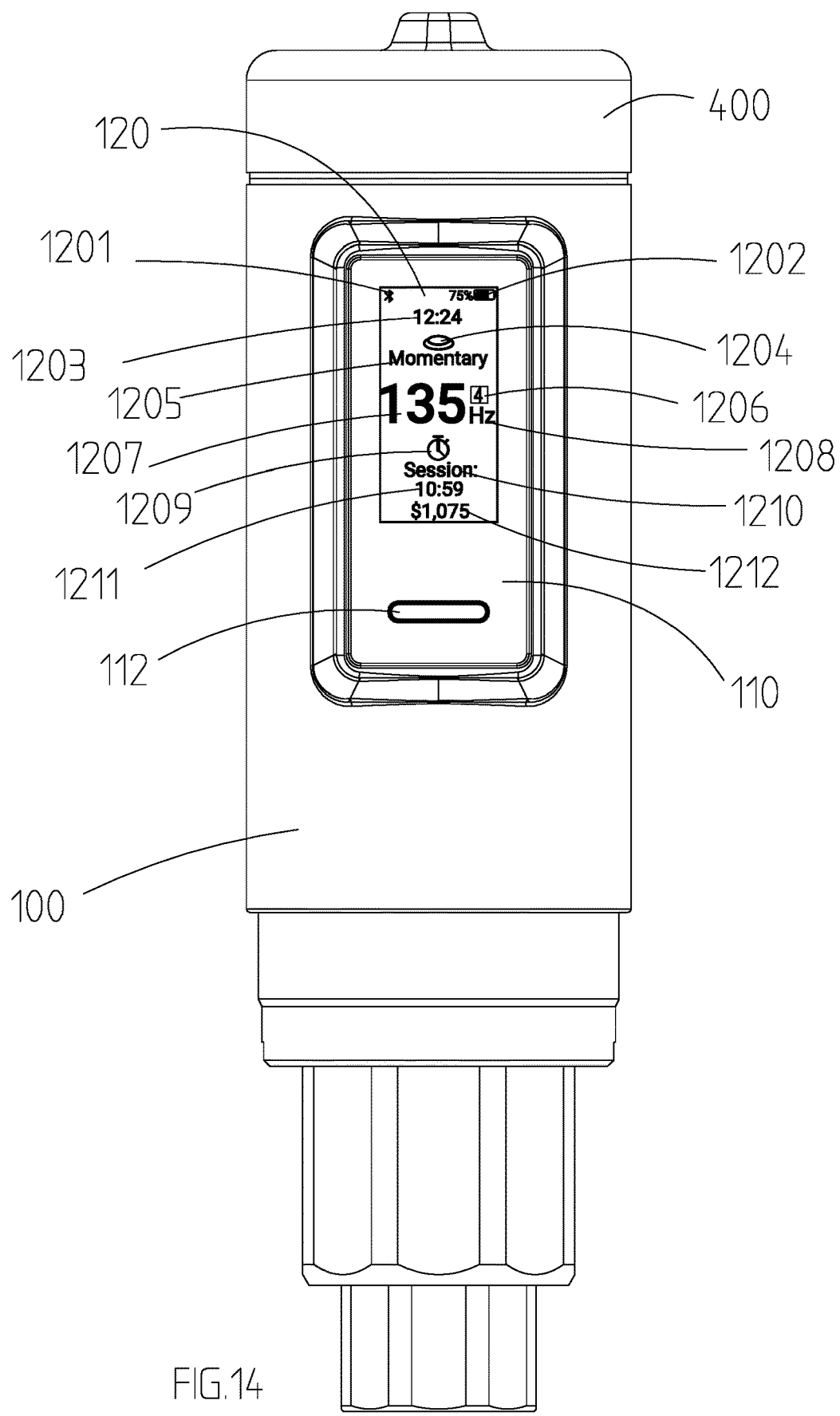
FIG. 14 is an enlarged top view of the touchscreen of the tattoo device of FIG. 1A.

As depicted in FIG. 14, display 120 may show:

- an icon or indicator 1201, indicative of the status of the Bluetooth connection, which may be on (icon present) or off (icon not present).
- an icon or indicator 1202, indicative of the battery life status, such as in percentage, or the expected lifetime left in hours or minutes. In some embodiments, the display may be a colored display and the icon for battery life may turn red when the battery capacity is below a threshold percentage.
- current time 1203, which may be absent if device 10 is not connected to APP 600 through Bluetooth connection.
- an icon or indicator 1204 indicative of the on/off status, or wireless connection status, of the foot pedal 500.
- an indicator 1205 indicative of the mode of operation of the foot pedal 500. For example, the sign "Momentary" may indicate that the motor 160 will be turned on when foot pedal 500 is pressed, and will stop when the foot pedal 500 is released. The sign "Maintain" may indicate that pressing and then releasing the foot petal 500 once will turn on motor 160 and motor 160 will continuously run until control circuit 130 receives a further command. Pressing and releasing the foot pedal 500 again will stop motor 160.

a number indicator 1206 indicative of the speed level. As depicted, the speed level is currently at level 4.

a number indicator 1207 indicative of the motor speed. As illustrated, the speed is 135 (Hz).

a number indicator 1208 indicative of the unit of the speed. As shown, the unit is Hz. This unit may also be needle cycle per second.

an icon 1209 indicative of a timer.

an indicator 1210 of the mode of time recordal. For example, three possible timer modes may be available:
1) Session mode: records the total time for an entire tattoo session. In this mode, the user manually starts and stops the timer.
2) Run mode: time is recorded only when the motor 160 is running or device 10 is on.
3) Hybrid mode: the timer is started and stopped manually by the user or automatically by operation of the motor. Further, the timer will suspect recording time when the motor 160 is off for more than a pre-selected time interval threshold. The pre-selected time interval threshold may be selected by the user.

a time indicator 1211 indicative the cumulative time of the tattoo session that is billable.

a fee indicator 1212 indicative of the total amount of fees currently incurred. The dollar amount of the fee may be calculated by multiplying the recorded session time and the hourly rate of the tattooist.

Device 10 may be configured to provide presets for various operation parameters and controls, as can be understood by those skilled in the art.

Figure 15:
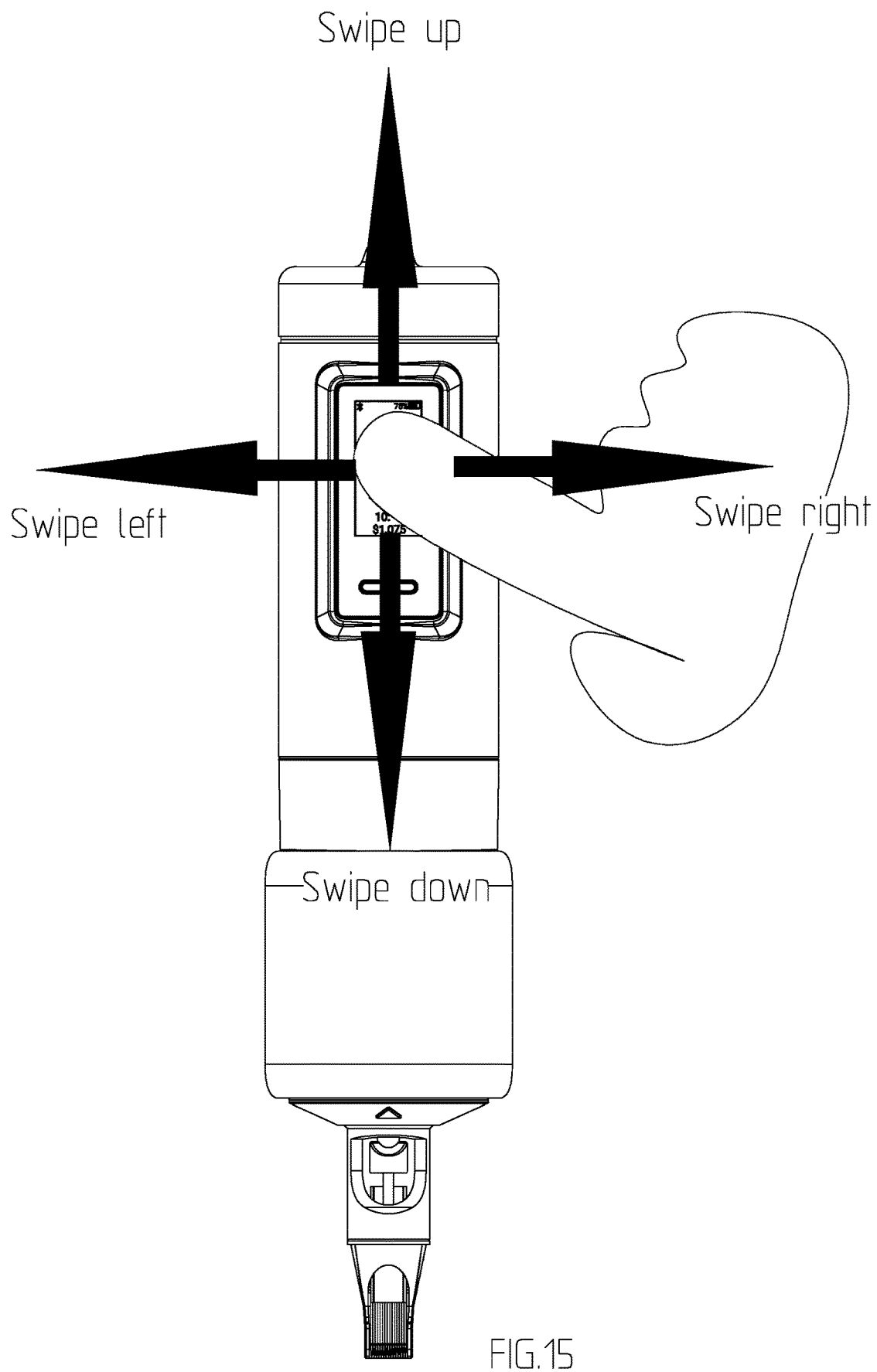
FIGS. 15-16 are views of the display and input screen of FIG. 14 with a user finger, illustrating possible finger gestures.

As illustrated in FIG. 15, a user may swipe her finger in four different directions, upwards, downwards, leftwards, or rightwards, in a designated area of the display 120, which is also a sensing surface 110 so the finger swipe direction may be detected. Each swipe direction may be associated with a speed control command. For example, upwards and rightwards swipe may increase the motor speed; and downwards and leftwards swipe may decrease the motor speed. An upwards swipe may increase the motor speed by a predefined increment. A downwards swipe may decrease the motor speed by the predefined increment. A rightwards swipe may increase the motor speed by one speed level, and a leftwards swipe may decrease the motor speed by one speed level. For example, the motor speed may be predefined and grouped into 4 to 6 different speed levels. It is also possible to circularly change the speed level within the predefined levels, such that, for example, when there are only 4 predefined levels, at level 4, a rightwards swipe would change the speed level to level 1 instead of level 5 which is not defined. In some embodiments, the four speed levels may be (1)—100 Hz; (2)—115 Hz; (3)—135 Hz; and (4)—140 Hz.

Figure 16:
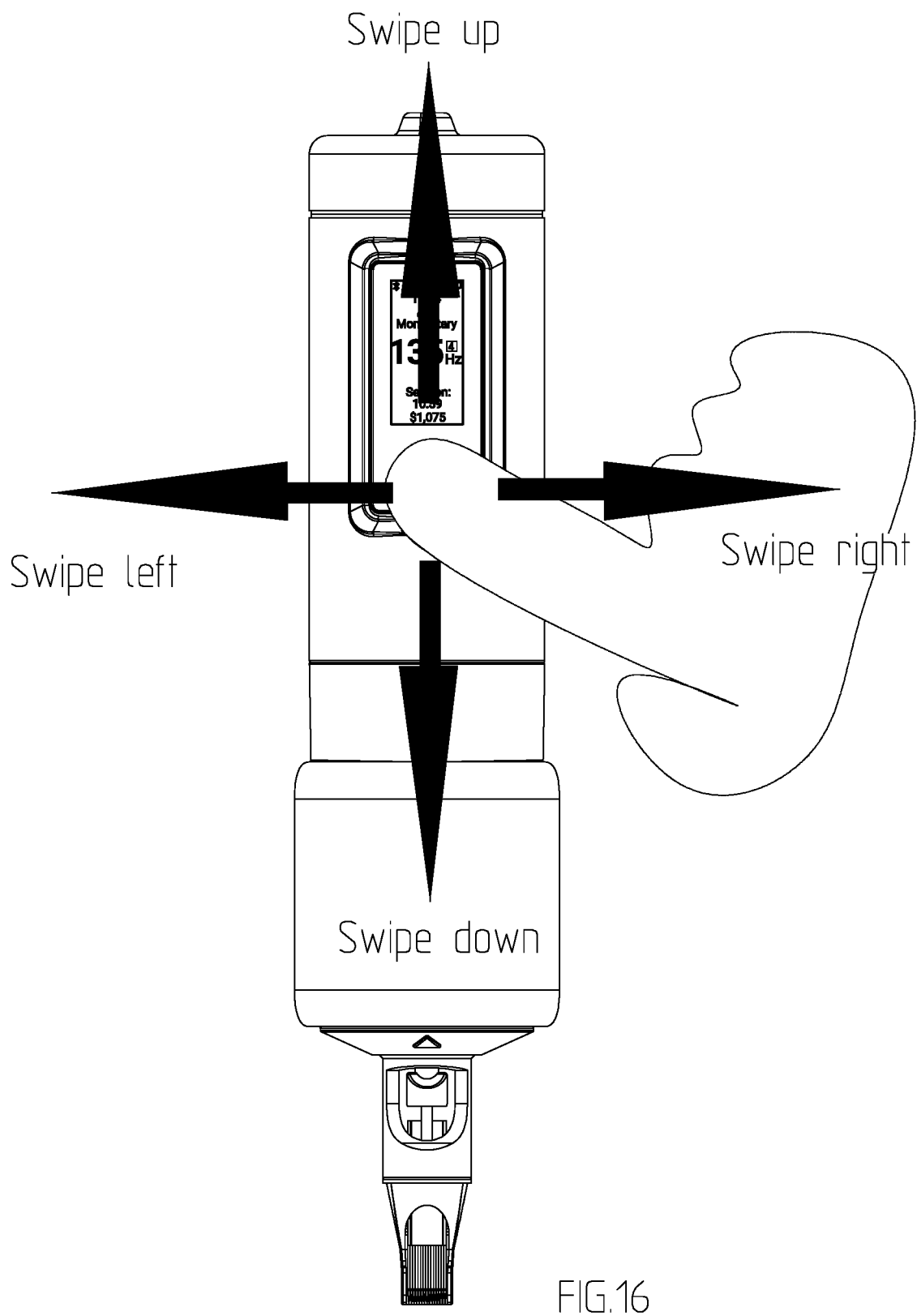

It is possible to swipe within the display region that shows the speed value. It is also possible to swipe outside this display region in order to adjust motor speed, as illustrated in FIG. 16. A hand gesture or finger swipe may include a finger touching the touchscreen and then dragging, sliding, scrolling, or flicking, or performing any like motion that can indicate a direction to the touch sensor under the sensing surface 110.

In some embodiments, a finger tap on the display region showing the speed value, or any other region, may stop or suspend operation of the motor 160. Another tap may restart the motor 160, and return the motor speed to the speed just before the stop, or up to a preset starting speed.

Continuously touching the touchscreen (i.e. press and hold) for a certain time period, such as 1.5 s, may start or stop the session timer. Alternatively, double tapping the speed value region may start or stop the session timer.

In some embodiments, the upper section 100 may include a metallic frame 165 for mounting and supporting the needle actuator 101 including motor 160 and the circuit boards for the control circuitry. The frame may be formed of an aluminum alloy. Aluminum alloy has the benefits of light weight so it is suitable for a handheld device, and good thermal conductivity so it can facility heat dispersion in the device. Frame 165 may have a generally cylindrical or tubular shaped section.

The battery protection circuit 430 may be configured to detect or measure the instantaneous output current and voltage of the battery 440 respectively, and to control discharging operation of the battery 440 accordingly. The battery protection circuit 430 can prevent fire or explosion caused by external short-circuiting through an external part connected to the battery, or by internal short-circuiting due to overcharging of the battery 440. The battery protection circuit 430 can also prevent overcharging and over-discharging of the battery 440, and thus increase the life span of battery 440 and increase the stability and safety of the device 10.

Figure 9A:
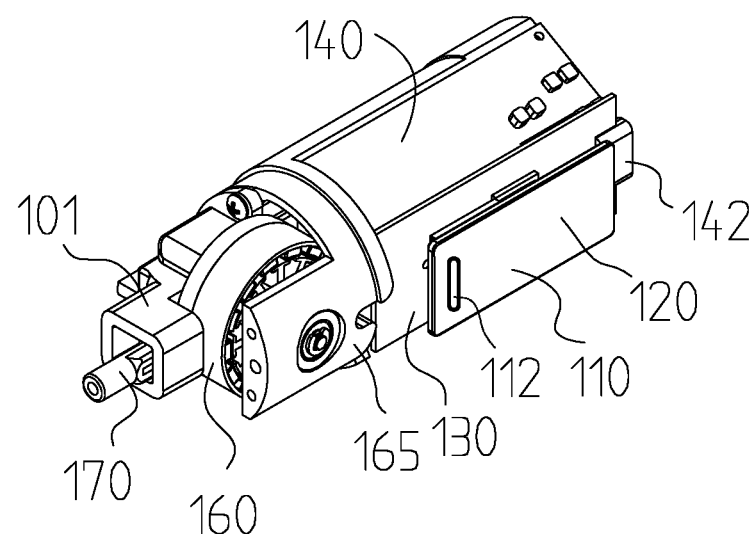
Figure 9B:
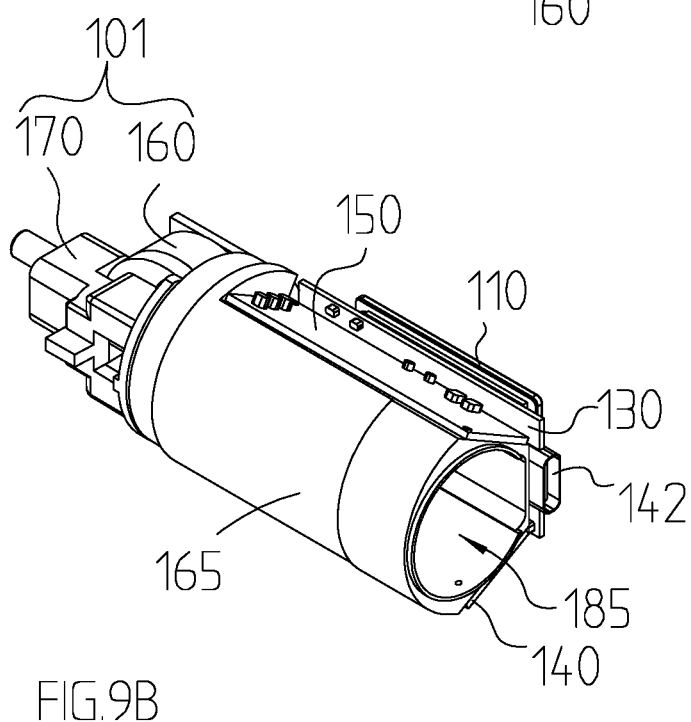
Figure 10:
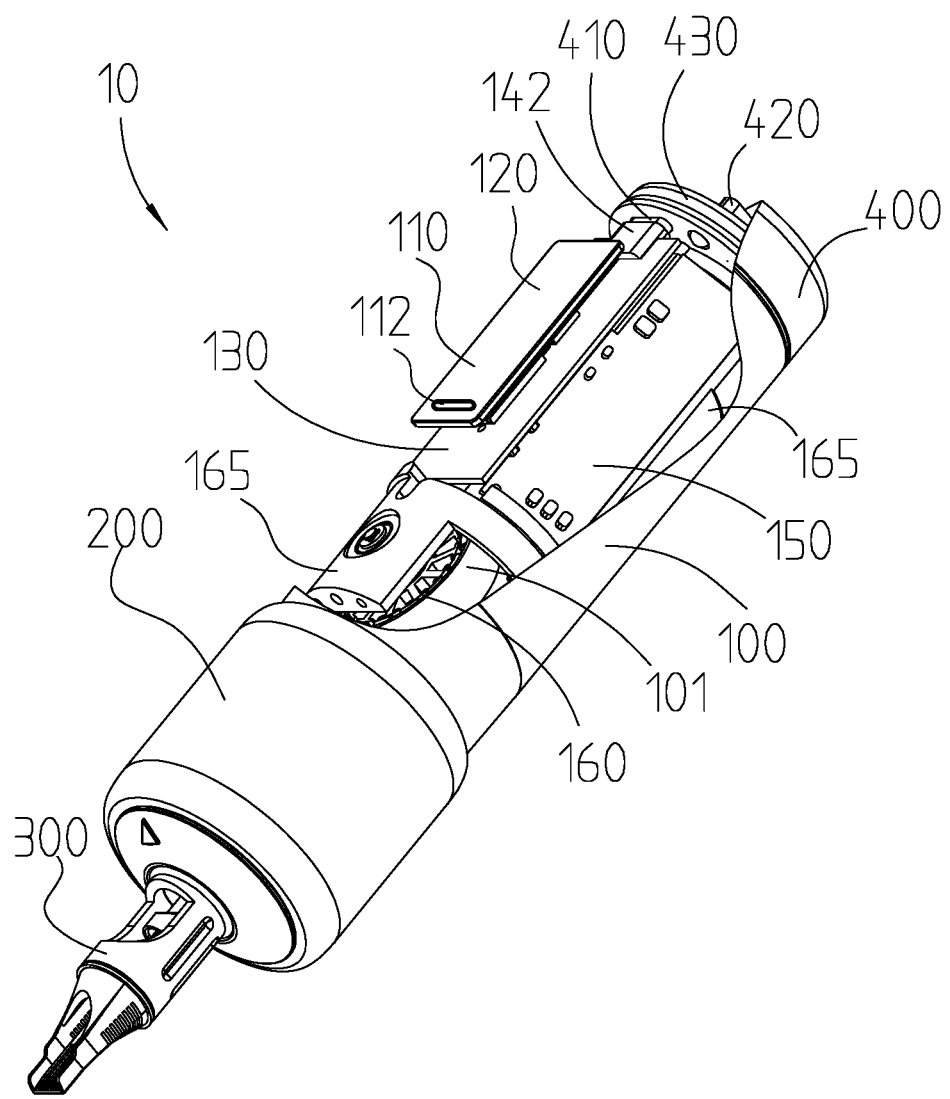
FIG. 10 is a cut-out perspective view of the device of FIG. 1A, showing internal arrangement of the battery pack, circuit boards, touchscreen, and needle actuator in the device.

As can be appreciated, a generally cylindrical handle or pen-shaped device is suitable for being held in a human hand and being manipulated. However, the cylindrical shape limits the size and shape of the circuit boards that can be mounted in the cylindrical body. To utilize the space available in the cylindrical body of device 10 efficiently or optimally, the circuit board(s) used in device 10 is (are) arranged around the cylindrical battery casing 450. In one example, as illustrated in FIGS. 9A, 9B and 10, three flat circuit boards may be arranged around casing 450. These circuit boards may each be formed on a rigid substrate. The three circuit boards provide the control unit 130, battery voltage boost converter 140, and motor driver circuit 150 thereon respectively, and for brevity will also be referred to as circuit board 130, circuit board 140, and circuit board 150 hereinafter.

Figure 5:
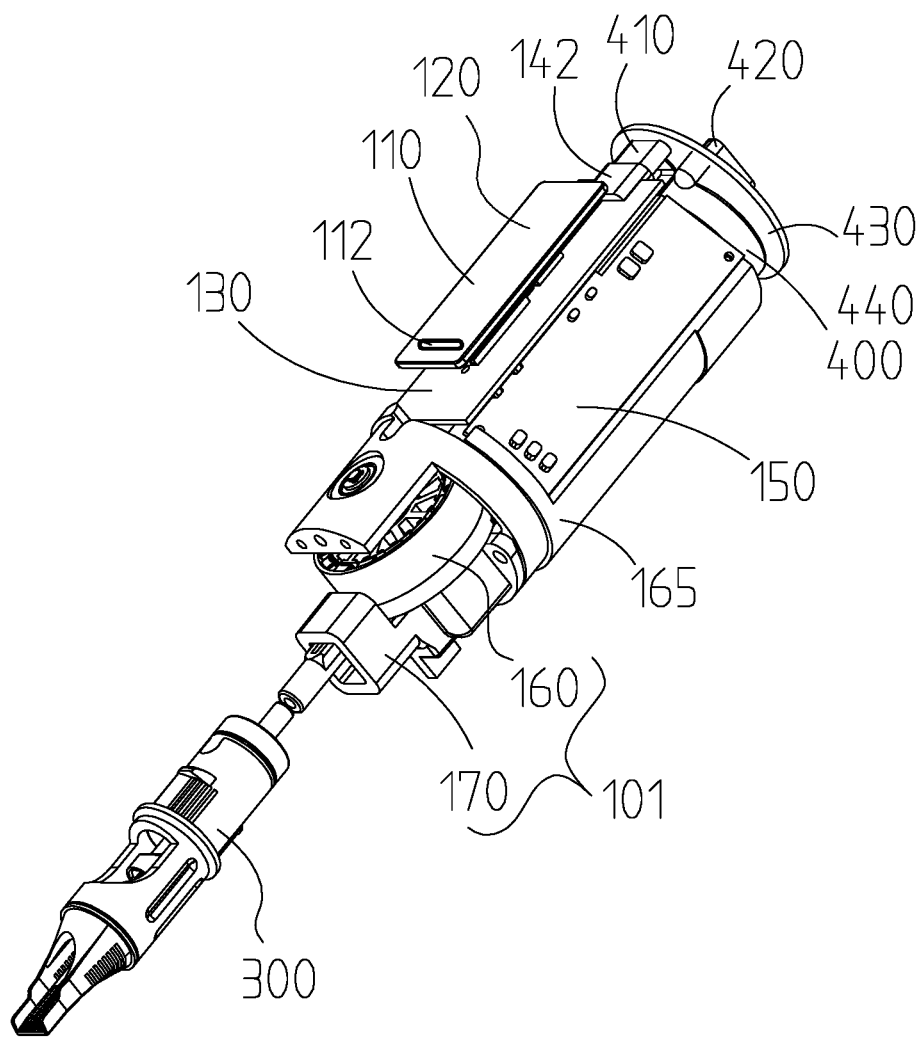
FIG. 5 is a perspective view of internal components in the tattoo device of FIG. 1A.

As better illustrated in FIGS. 4, 5 and 10, the discharging port 410 of battery pack 400 is coupled to a USB type C female connector 142 mounted on circuit board 130. In other words, circuit board 130 includes a USB type C receptacle for detachably receiving therein the USB type C connector 410 of the battery pack 400. Conveniently, connector 142 can provide both power to the control unit 130 and a communication port for communicating signals between the control unit 130 and an external device connected to the control unit 130 directly or indirectly through the connector 142. For example, connector 142 may be used for testing, adjustment and calibration purposes during or post manufacture, and for uploading or updating software stored in the memory of the control unit 130.

As illustrated in FIGS. 9A and 9B, the three circuit boards 130, 140, 150 may be fixedly mounted on frame 165, and may be affixed in position using screws or an adhesive.

Figure 6:
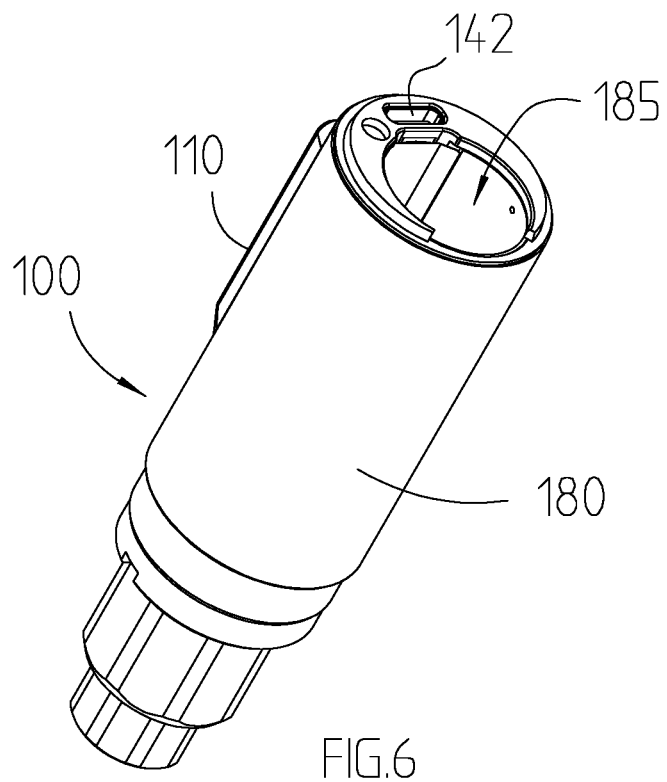
FIG. 6 is a perspective view of the upper section of the tattoo device of FIG. 1A, with the battery pack removed.
Figure 7:
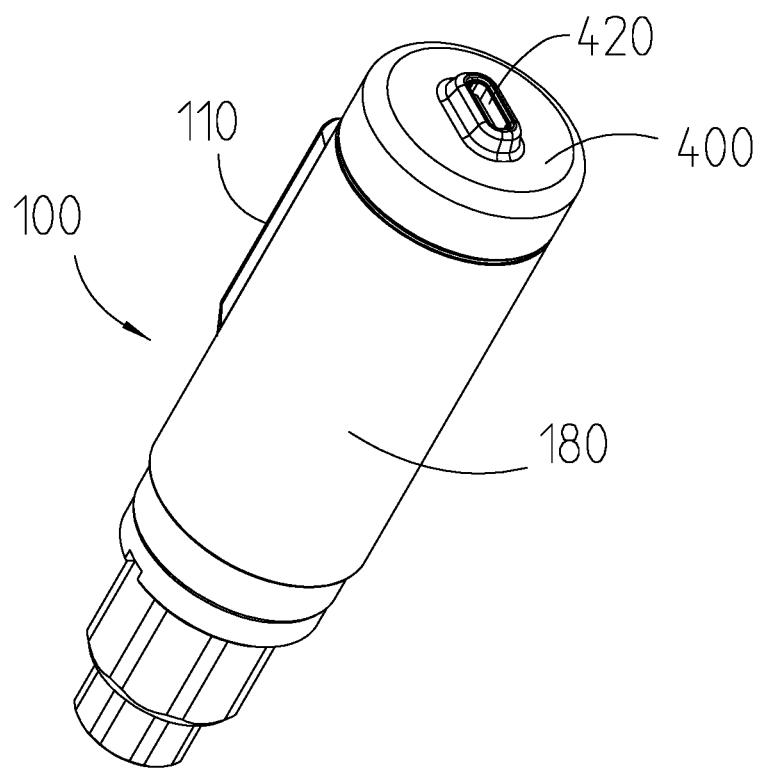
FIG. 7 is a perspective view of the upper section of tattoo device of FIG. 1A with the battery pack.
Figure 8:
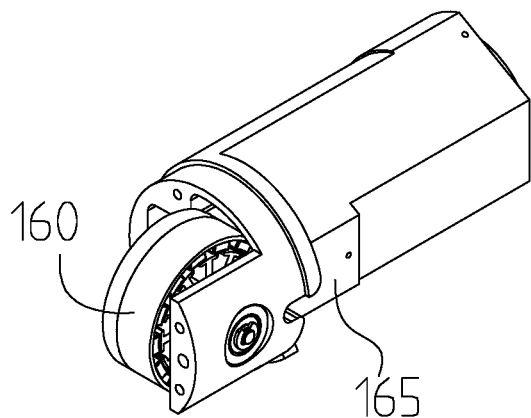
FIGS. 8 and 9A-9B are partial, cut-out views of the actuator, the housing frame, touchscreen, and the circuitry boards for the control circuitry of the device of FIG. 1A.

As depicted in FIGS. 6 and 9B, frame 165 may include a cylindrical section defining a chamber 185 for housing or mounting the battery pack 400.

In different embodiments, one or more flexible or deformable circuit boards may be used to provide the control circuitry or other circuits in the device 10. For example, a single flexible circuit board may be used to provide all circuits needed in the device 10.

In an embodiment, frame 165 may be clamped within casing 180. Casing 180 may include an upper portion and lower portion, which are coupled to each other by threaded connection, and thus encasing the frame 165 and other components such as the circuit board(s) and the actuator. Frame 165 may also be mounted in casing 180 by screws or other affixing devices.

FIG. 17A to 17L illustrates possible information displayed on the display 120.

In some embodiments, the home page is as illustrated in FIG. 14. At the home page, double-click on button 112 brings up the navigation page on the display 120 for user settings, as illustrated in FIGS. 17A to 17D. The user can scroll through the selectable setting items and select a particular setting item to set the corresponding setting, by touching the particular item or press button 112 once.

Figure 17A:
FIGS. 17A-17L are different screen displays shown on the display and input screen of FIG. 14.
Figure 17B:
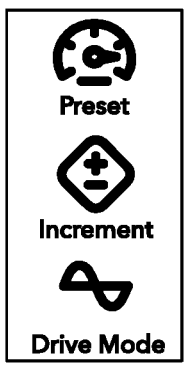
Figure 17C:
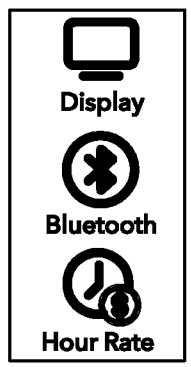
Figure 17D:
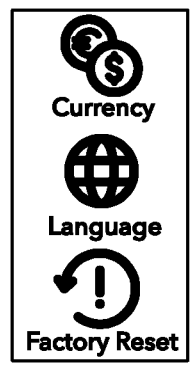
Figure 17E:
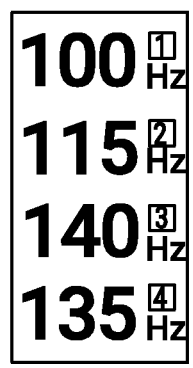
Figure 17F:

For example, selecting the "Preset" icon on FIG. 17B would bring up the page shown in FIG. 17E, which shows 4 preset motor speed levels and their corresponding speed in Hz. If the user press the level 1 line in FIG. 17E, the display 120 will switch to display a screen as shown in FIG. 17F, which allows the user to adjust the speed setting for speed level 1. The user may press the "+" or "−" icon shown on the screen to increase or decrease the speed setting for level 1. For example, one quick press may increase or decrease the speed value by 1 Hz, and pressing continuously may continue to increase or decrease the speed value, and increasingly more quickly as the press time becomes longer.

Figure 17G:
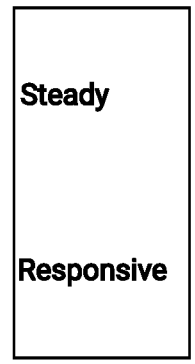

As another example, pressing the Drive Mode icon on the screen in FIG. 17B may bring up the screen shown in FIG. 17G, which shows two modes: Steady or Responsive. Selecting the "Steady" mode would cause the control circuitry to operate in a closed-loop control mode for controlling the motor 160. Selecting the "Responsive" mode causes the control circuitry to operate in open-loop control mode.

Figure 17H:
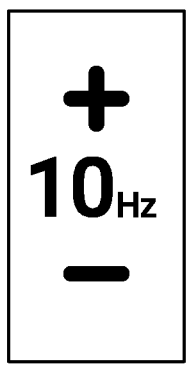

Selecting "Increment" in FIG. 17B brings up the page in FIG. 17H, which displays the previously set speed increment, e.g. 10 as depicted, which may be changed by pressing the "+" or "−" sign.

Figure 17I:
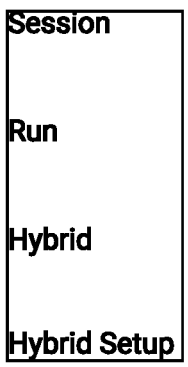
Figure 17J:
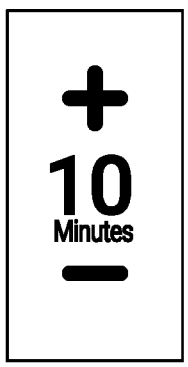

Selecting the "Timer" item on FIG. 17A brings up the page in FIG. 17I, for setting the session time recordal mode as discussed above. Selecting the Hybrid Setup will bring up the setting page shown in FIG. 17J, for setting the pre-selected time interval threshold described herein. As shown in FIGS. 17C and 17D, one or more of Display settings, Bluetooth connection settings, the hourly rate of the tattooist, the currency or language used on the invoices may also be set by the user, or the user may reset all settings to the factory default settings. With these settings, the example device is convenient to use in different regions and countries.

Selecting the "Checkout" item on the home page in FIG. 17A brings up a new page (not shown) for complete the billing for a completed tattoo session.

Figure 17K:
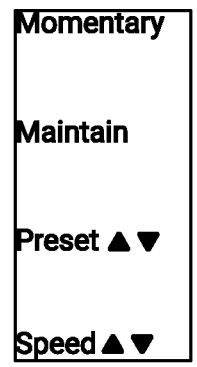

Selecting "Pedal" in FIG. 17A would bring up a setting page as shown in FIG. 17K for the pedal settings. The current setting selection may be highlighted, and the user may select another setting to set. In some embodiments, a foot pedal 500 may be wirelessly connected to device 10. The foot pedal 500 may be a dual foot pedal. For example, one of the two pedals (e.g. the right pedal) may be associated with increasing of the motor speed and the other of the two pedals (e.g. the left pedal) may be associated with decrease of the motor speed. When both pedals are pressed, the control circuitry of device 10 may temporarily suspend or restart motor rotation. The association of the pedals and motor operation commands may be set by a user, such as through the "Pedal" setting pages. The "Preset" setting shown in FIG. 17K may be selected so that when a single pedal of a dual-pedal device is pressed, the motor speed is increased or decreased by one speed level. When the "Speed" setting in FIG. 17K is selected, pressing a single pedal may increase or decrease the speed by a preselected increment, instead of by a preset level. The dual foot pedal may be in communication with the control circuitry through the wireless transceiver and provide control command signals to the control circuitry in response to the pedal(s) being pressed by a foot of a user. Foot pedal 500 may be connected to device 10 through a wireless connection, such as Bluetooth or 2.4G wireless connection.

In some embodiments, device 10 may also be configured to receive voice control or voice commands, as described in US Patent Application Publication No. US 2021/0060325 by Long Xiao, the entire contents of which are incorporated herein by reference. If voice control is provided, the settings for voice control may also be provided in the user interface such as in the setting page illustrated in FIG. 17K. APP 600 may also communicate with device 10 through a Bluetooth connection.

Figure 17L:
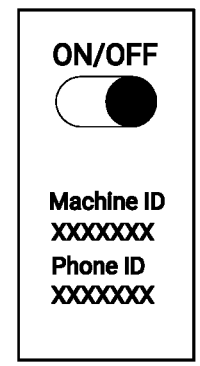

On a setting page as shown in FIG. 17C, the settings for "Display", "Bluetooth" and "Hourly rate" may be selected and set. When the Bluetooth setting is selected, a setting page as shown in FIG. 17L may be presented. The "ON/OFF" icon switches the Bluetooth component in device 10 on or off. In different embodiments, device 10 may be connected to foot pedal switches, mobile phones, or other portable computer or control devices, through the Bluetooth connection. The Bluetooth connection, as a whole or with any specific other device, can be turned on or off through the setting page shown in FIG. 17C. For example, the setting pages may be configured so that selecting "Bluetooth" or the Bluetooth icon shown in FIG. 17C will bring up a new page showing selectable ON/OFF buttons. When the ON or OFF button or icon is selected, a confirmation screen is shown to confirm that the device's Bluetooth connection is now on or off. Devices with Bluetooth capabilities may be paired with device 10 and the paired devices may be listed on a page when the Bluetooth icon on FIG. 17C is selected. Device 10 may be configured to provide any known Bluetooth functionalities such as those provided by existing mobile phones.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A pen-shaped handheld tattoo device, comprising:
an elongated body having a pen shape and comprising
a grip section, comprising a coupling end configured to removably couple with a needle module comprising one or more needles, and
an upper section above the grip section, the upper section comprising a needle actuator for actuating the one or more needles through a shaft extending through the grip section, and a battery power source for supplying electrical power to the needle actuator;
a user interface on the upper section, the user interface comprising a display and a touch sensor for detecting finger gestures of a user including swipe directions; and
a control circuitry in the upper section for controlling the power supplied to the actuator by the battery power source based on user input received through the user interface,
wherein the needle actuator comprises an electrical motor and the control circuitry is configured to adjust a speed of the motor based on a detected finger gesture including a swipe direction of the detected finger gesture.

2. The handheld tattoo device of claim 1, wherein the user interface comprises a touchscreen providing both a display surface and a touch sensing surface.

3. The handheld tattoo device of claim 1, wherein the battery power source comprises a tubular casing for receiving a battery therein.

4. The handheld tattoo device of claim 3, wherein the control circuitry comprises at least one circuit board mounted around the tubular casing.

5. The handheld tattoo device of claim 4, wherein the at least one circuit board comprises three flat circuit boards surrounding the tubular casing.

6. The handheld tattoo device of claim 4, wherein the at least one circuit board comprises a deformable circular circuit board curved around the tubular casing.

7. The handheld tattoo device of claim 1, wherein the control circuitry comprises a processor, and a processor readable medium storing thereon processor-executable instructions.

8. The handheld tattoo device of claim 7, wherein the instructions when executed by the processor cause the control circuitry to:
display information on the display;
receive user input through the user interface;
update the information displayed on the display in response to user input received through the user interface;
control operation of the device based on the user input.

9. The handheld tattoo device of claim 8, wherein the user input comprises finger gestures detected through the touch sensor.

10. The handheld tattoo device of claim 9, wherein the control circuitry is configured to control an operation speed of the actuator based on a detected finger gesture, wherein the control circuitry causes the speed to increase in response to detecting a finger swipe in a first swipe direction, or to decrease in response to detecting a finger swipe in a second swipe direction opposite to the first swipe direction.

11. The handheld tattoo device of claim 1, wherein the user interface comprises a physical or virtual home button or key.

12. The handheld tattoo device of claim 1, wherein the touch sensor is adjacent to the display.

13. The handheld tattoo device of claim 1, wherein the touch sensor comprises a plurality of touch sensors providing a continuous sensing surface or discrete sensing surfaces.

14. The handheld tattoo device of claim 1, wherein the control circuitry is configured to increase or decrease the speed of the motor by a preselected amount based on the swipe direction of the detected finger gesture.

15. The handheld tattoo device of claim 1, wherein the touch sensor is configured to detect if the swipe direction is an upward direction, a downward direction, a leftward direction, or a rightward direction.

16. The handheld tattoo device of claim 1, wherein the swipe direction is detectable in a display area of the display, or within a defined sensing area outside the display area.

17. The handheld tattoo device of claim 1, wherein the display is controlled by the control circuitry to display one or more of a status of the motor, an operation status of the device, a user setting for the device or the motor, and time information, wherein the status of the motor comprises the speed of the motor.

18. The handheld tattoo device of claim 1, wherein the user interface is controlled by the control circuitry to display user selectable items on the display and to receive user selection through the touch sensor.

19. The handheld tattoo device of claim 1, wherein the control circuitry comprises a primary control circuit, a voltage boost converter circuit, and a motor driver circuit.

20. The handheld tattoo device of claim 19, wherein the primary control circuit comprises a wireless transceiver and a controller.

21. The handheld tattoo device of claim 20, wherein the control circuitry is configured to communicate with a dual-foot pedal switch through the wireless transceiver, the dual-foot pedal switch providing control signals to the control circuitry in response being pressed by a user's foot.

22. The handheld tattoo device of claim 19, wherein the motor is a commutatorless direct-current motor, and the motor driver circuit is configured to detect or calculate an instantaneous speed of the motor and transmit a signal indicative of the speed to the primary control circuit.

23. The handheld tattoo device of claim 1, comprising a frame in the upper section, wherein the motor and the control circuitry are both mounted on the same frame.

24. The handheld tattoo device of claim 1, wherein the grip section comprises a handle detachably coupled to the upper section.

25. The handheld tattoo device of claim 1, wherein the battery power source comprises a battery pack detachable from the upper section.

26. The handheld tattoo device of claim 25, wherein the battery pack is detachably mounted at a terminal end of the upper section, and the battery pack comprises a tubular casing for receiving and housing a battery therein and a battery management circuit for managing at least discharging of the battery.

27. The handheld tattoo device of claim 26, wherein the upper section comprises a USB type-C receptacle, and the battery pack comprises a USB type-C connector detachably received in the receptacle.

* * * * *